US006337319B1

United States Patent
Wang (10) Patent No.: US 6,337,319 B1
(45) Date of Patent: *Jan. 8, 2002

(54) μ-SELECTIVE OPIOID PEPTIDES (76) Inventor: Wuyi Wang, 2297 Frenette, St-Laurent, Québec (CA), H4R 1M3

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/718,585

(22) PCT Filed: Aug. 14, 1996

(86) PCT No.: PCT/SE96/01011

§ 371 Date: Oct. 2, 1996

§ 102(e) Date: Oct. 2, 1996

(87) PCT Pub. No.: WO97/07130

PCT Pub. Date: Feb. 27, 1997

(30) Foreign Application Priority Data

Aug. 18, 1995 (SE) ................................. 9502877
Nov. 7, 1995 (SE) ................................. 9503924

(51) Int. Cl.⁷ .......................... A61K 38/07; C07K 5/10; C07K 5/107
(52) U.S. Cl. .......................... 514/18; 530/302; 530/330; 530/333
(58) Field of Search ................................ 530/330, 333, 530/302; 514/18

(56) References Cited

U.S. PATENT DOCUMENTS 5,312,899 A    5/1994    Schiller ...................... 530/331

FOREIGN PATENT DOCUMENTS

WO    WO 95/22557    8/1995
WO    WO95/22557  *  8/1995

OTHER PUBLICATIONS

Filler, R 'Biologically Active Fluorochemicals', J. of Fluorine Chemistry, vol. 33, pp. 361–375 (1986).*
Bodanszky, *Principles of Peptide Synthesis*, Berlin:Springer–Verlag (1984).
Budd, "Analgesis Drugs" in *International Encyclopedia of Pharmacology and Therapeutics*, eds. N.E. Williams and H. Wilkinson, Oxford:Pergammon (1983), 51–63.

*The Peptides*, New York:Adacemic Press (1979).
Lord, et al., "Endogenous Opioid Peptides: Multiple Agonists and Receptors," *Nature* 267:495–499 (1977).
Martin, et al., "The Effects of Morphine– and Nalorphine–Like Drugs in the Nondependent and Morphine–Dependent Chronic Spinal Dog," *J. Pharmacol. and Exper. Ther.* 197:517–532 (1976).
Schiller, et al., "Insulfated C–Terminal 7–Peptide of Cholecystokinin: A New Ligand of the Opiate Receptor," *Biochem. and Biophys. Res. Comm.* 85: 1332–1338 (1978).
Schiller, et al., "New Types of Opioid Peptide Analog Showing High μ–Receptor Selectivity and Preference for Either Central or Peripheral Sites," *Peptides 1988, Proceedings of the 20th European Peptide Symposium*, 613–615 (1988).
Silbert, et al., "Analgesic Activity of a Novel Bivalent Opioid Peptide Compared to Morphine Via Different Routes of Administration," *Agents and Actions* 33:382–387 (1991).
Siegmund, et al., "A Method for Evaluating Both Non–Narcotic and Narcotic Analgesics," *Proc. Soc. Exp. Biol. Med.* 95:729–731 (1957).
Woolfe, et al., "The Evaluation of the Analgesic Action of Pethidine Hydrochloride (Demerol)," *J. Pharmacol. and Exp. Ther.* 80:300–307 (1944).
International Search Report for Swedish appls 9502877–5 and 9503924–4 (priority appls. of PCT/SE96/01011).#jf139##

Primary Examiner—Christopher S. F. Low
Assistant Examiner—Anish Gupta
(74) Attorney, Agent, or Firm—Michael A. Sanzo; Pillsbury Winthrop LLP

(57) ABSTRACT

This invention relates to novel opioid peptides for the treatment of pain as well as a method for the preparation thereof and pharmaceutically acceptable compositions comprising these peptides. The invention also relates to methods for controlling pain in patients using compositions of the invention and the use of said compounds in the preparation of formulations effective in pain treatment. The peptides of this invention have a high degree of selectivity for the μ-opioid receptor. The peptides of the present invention are particularly well-suited as analgesic agents acting substantially on peripheral μ-opioid receptors. Because these peptides act peripherally, they substantially avoid producing side effects normally associated with central analgesic action.

15 Claims, 5 Drawing Sheets

1B  Measurement of analgesic activity in the hot plate assay of compound #1B and compound #2B

Fig. 3

1A  Measurement of analgesic activity in the hot plate assay of compound # 1A

μ-SELECTIVE OPIOID PEPTIDES

CROSS REFERENCE TO RELATED APPLICATIONS

The present application represents U.S. national stage of internationl application PCT/SE96/01011, with an international filing date of Aug. 14 1996. The international application was published in English under Article 22(2) of the PCT. It claims priority to Swedish application 9502877-5 filed on Aug. 18, 1995, and to Swedish application 9503924-4 filed on Nov. 7, 1995.

FIELD OF THE INVENTION

The present invention relates to opioid-like peptide compounds. More particularly, it relates to opioid-like peptide compounds that exhibit peripheral analgesic activity and selectivity for the μ subtype of opioid receptors.

BACKGROUND OF THE INVENTION

Many endogenous peptides of mammalian and amphibian origin bind to specific opioid receptors and elicit an analgesic response similar to classic narcotic opiates. Many different types of opioid receptors have been shown to coexist in higher animals. For example, see W. Martin et al., *J. Pharmacol. Exp. Ther.*, 197, p. 517(1975); and J. Lord et al., *Nature(London)* ,257 p. 495(1977). Three different types of opioid receptors have been identified. The first, δ, shows a differentiating affinity for enkephalin-like peptides. The second, μ, shows enhanced selectivity for morphine and other poly-cyclic alkaloids. The third, κ, exhibits equal affinity for either group of the above ligands and preferential affinity for dynorphin. In general, the μ-receptors seem to be more involved with analgesic effects. The δ-receptors appear to deal with behavioral effects, although the δ and the κ-receptors may also mediate analgesia.

Each opioid receptor, when coupled with an opiate, causes a specific biological response unique to that type of receptor. When an opiate activates more than one receptor, the biological response for each receptor is affected, thereby producing side effects. The less specific and selective an opiate may be, the greater the chance of causing increased side effects by the administration of the opiate.

In the prior art, opiates, opioid peptides, and analogs thereof, have either failed to demonstrate, or have demonstrated a limited degree of selectivity for the type of receptor, or receptors, to which they bind.

Opiates can cause serious and potentially fatal side effects. Side effects such as respiratory depression, tolerance, physical dependence capacity, and precipitated withdrawal syndrome are caused by nonspecific interactions with central nervous system receptors. See K. Budd, In *International Encyclopedia of Pharmacology and Therapeutics*; N. E. Williams and H. Wilkinson, Eds., Pergammon: (Oxford), 112, p.51 (1983). Therefore, opioid analgesics acting principally through opioid receptors in the peripheral nervous system would not be expected to cause similar unwanted side effects as those side effects associated with opioid analgesics affecting the central nervous system.

To date, one of the few classes of agents known to exert peripheral analgesic effects are non-steroidal anti-inflammatory agents, such as aspirin, ibuprofen, and ketorolac. These agents do not interact with opioid receptors but are known to inhibit cyclooxygenase and attenuate prostaglandin synthesis. These weak analgesics do not have centrally mediated side effects, but they can cause other side effects such as ulcerations of the gastro-intestinal tract.

It was thought that non-polar peptides pass more easily into the central nervous system than polar peptides by traversing the blood-brain barrier. It has been published that TAPP(H-Tyr-D-Ala-Phe-Phe-NH$_2$) exhibited antinociceptive properties both peripherally and centrally (P. Schiller et al., *Proceedings of the 20$^{th}$ European Peptide Symposium*, 1988). In contradiction, it has been found by the present inventor that this tetrapeptide does not act centrally even at doses of 100 mg/kg.

It is an object of the invention to provide opioid-like peptide compounds which act peripherally but substantially avoid the unwanted side effects associated with conventional peripherally acting analgesics. It is a further object to provide peptide compounds which bind selectively to the μ-opioid receptor.

SUMMARY OF THE INVENTION

The present invention provides novel peptide compounds which act peripherally and are selective for μ-opioid receptors, the compound represented by formula (1):

and salts, derivatives and analogues thereof wherein,

R$_1$ is Tyr or 2',6'-dimethyltyrosine, or an analog or derivative thereof;

R$_2$ is D-Ala or D-Arg;

R$_3$ is Phe(p-F);

R$_4$ is Phe or Phe(p-F);

X is H or C$_{1-6}$alkyl; and

Y and Z are independently H, aralkyl or C$_{1-6}$alkyl.

In another aspect of the invention, there is provided pharmaceutical compositions comprising a compound of formula (1) in admixture with a pharmaceutically acceptable carrier and/or a second therapeutically active agent.

In a further aspect of the invention, there is provided a method of treating pain comprising administering to a mammal in need of such treatment a pharmaceutically effective amount of a compound of formula (1).

In a further aspect of the invention, there is provided the use of a compound of formula (1)for the manufacture of a medicament for treating pain.

DESCRIPTION OF THE INVENTION

The following common abbreviations are used throughout the specification and in the claims:

Ala—alanine
Arg—arginine
Phe—phenylalanine
Ser—serine

Tyr—tyrosine
TAPP—H-Tyr-D-Ala-Phe-Phe-NH$_2$
GPI—guinea pig ileum
MVD—mouse vas deferens
Phe(p-F)—para-fluoro phenylalanine
HOBT—N-hydroxybenzothiazole
BOP—benzotriazolyl-N-oxy-tris(dimethylamino) phosphoniumhexafluorophosphate
DMF—dimethylformamide
TFA—trifluoroacetic acid
tBU—tert-butyl
Pmc—2,2,5,7,8 pentamethylchroman-6-sulfonyl
FMOC—9-fluorenylmethyloxycarbonyl
PBQ—phenyl-p-benzoquinone The term "ED$_{50}$" as shown in table 1 for the PBQ writhing assays is defined as the dose of drug which induces a 50% reduction in the number of writhes observed compared to the control. The term "K$_i$" in table 1 for the binding assay is the inhibition constant of the known μ-receptor ligand DAMGO and δ-receptor ligand DADLE. The term "K$_i^\delta$/K$_i^\mu$" is a value used to indicate selectivity. This ratio represents the relationship of the affinities of opioid peptides for binding to the μ- and δ-receptors.

Compounds of the present invention are represented by formula (1):

(1)

and salts, derivatives and analogues thereof.

X is H or methyl and is preferably H.

R$_1$ is Tyr or 2',6'-dimethyltyrosine, and is preferably Tyr. The alpha-amino group of R$_1$ is substituted with X to form an amino group when X is H or an alkylamino group when X is methyl.

R$_2$ is D-Ala or D-Arg, and is preferably D-Ala.

R$_3$ is Phe(p-F).

R$_4$ is Phe or Phe(p-F), and is preferably Phe.

Y and Z are independently H; aralkyl, such as benzyl; and C$_{1-6}$alkyl, such as methyl. Preferably Y and Z are both H.

Compounds of the invention include but are not limited to:

Compound #1B H-Tyr-D-Ala-Phe(p-F)-Phe(p-F)-NH$_2$;
Compound #1C H-Tyr-D-Ala-Phe(p-F)-Phe-NH$_2$;
Compound #2B H-Tyr-D-Arg-Phe(p-F)-Phe(p-F)-NH$_2$; and
Compound #2C H-Tyr-D-Arg-Phe(p-F)-Phe-NH$_2$.

In a preferred embodiment, the compounds of the invention are selected from the group consisting of
Compound #1C H-Tyr-D-Ala-Phe(p-F)-Phe-NH$_2$; and
Compound #2C H-Tyr-D-Arg-Phe(p-F)-Phe-NH$_2$.

In a more preferred embodiment, the compound of the invention is
Compound #1C H-Tyr-D-Ala-Phe(p-F)-Phe-NH$_2$.

The amino acid derivative 2',6'-dimethyltyrosine (Dmt) may be substituted for tyrosine in the opioid peptide compounds. Experiments have shown that the substitution of Dmt for tyrosine at the R$_1$ position, the first amino acid residue in general formula 1, enhances the potency of the opioid peptide at the μ-receptor up to 2 orders of magnitude. The selectivity for the μ-receptor increases when the compound includes Dmt at the R$_1$ position. This substitution causes a corresponding shift in the ratio of binding inhibition constants to reflect the increased μ-receptor selectivity.

The opioid activity of the peptides was assessed in vitro using the guinea pig ileum (GPI) longitudinal muscle preparation and their antinociceptive activity was determined in vivo in PBQ induced writhing models (peripheral activity) and in two hot-plate tests (central activity) in rodents. The analgesic activity of the compound of the invention was also evaluated in the tal flick assay. The tail flick assay is used to evaluate the central analgesic activity of the compound. Comparison of the activities of compounds of the invention in the writhing, hot-plate, and tail flick assays demonstrated that the analgesic effects were predominantly mediated in the periphery. Peripheral analgesia was shown by a high potency in the writhing test coupled with a low potency in the hot-plate test or the tail flick test.

PBQ (phenyl-p-benzoquinone) induced writhing in mice is an assessment of both central and peripheral analgesia. For experimental protocol see Sigmund et al., *Proc. Soc. Exp. Biol. Med.*, 95, p. 729(1957) which is incorporated herein by reference. Central analgesia is determined by the inhibition of a hot-plate response in mice. For experimental protocol see G. Wolfe and A. MacDonald, *J. Pharmacol. Exp. Ther.*, 80, p.300 (1944) which is incorporated herein by reference. Assays measuring opioid receptor binding affinities for μ and δ receptors as well as the GPI assay were determined through experimental protocol set out in Schiller et al., *Biophys. Res. Commun.*, 85, p.1322 (1975) incorporated herein by reference.

The compounds of the present invention can be produced by methods well known in the art of peptide chemistry. For example, see *Principle of Peptide synthesis*, Bodansky M., Spinger-Verlag, Berlin, Heidelberg, New York, Tokyo 1984 or *The Peptides, Analysis, Synthesis, Biology*, edited by Erhard Gross and Johannes Meienhofer, Academic Press 1979.

The compounds of the present invention were prepared using solid phase synthesis as outlined below according to procedures established in the art of peptide synthesis. Commercially available para-fluoro-phenylalanine (Phe(p-F)) was employed at the appropriate step of synthesis. 2',6'-dimethyltyrosine may also be incorporated in the synthesis and is prepared according to established chemical synthesis techniques.

Pharmaceutically acceptable salts of the peptides of this invention may be formed conventionally by reaction with an appropriate acid. Suitable add addition salts may be formed by the addition of acids such as hydrochloric, hydrobromic, phosphoric, acetic, fumaric, salicylic, citric, lactic, mandelic, tartaric, oxalic, methanesulphonic, and other suitable acids known to persons skilled in the art.

The present invention also provides for pharmaceutical compositions. Suitable compositions have a pharmaceutically effective amount of compounds of the invention, or pharmaceutically acceptable salts thereof, in admixture with a pharmaceutically acceptable carrier or adjuvant. A therapeutically effective amount of a peptide of the invention and a pharmaceutically acceptable carrier substance (e.g. magnesium carbonate or lactose) can be formulated to form a therapeutic composition, such as (i) a pill, tablet, capsule, or liquid for oral administration to a patient; (ii) a liquid or an ointment capable of being administered by inhalation, transdermally, nasally, rectally or sublingually; (iii) a liquid capable of being administered intravenously, parenterally, subcutaneously or intraperitoneally; or (iv) an oral or a parenteral sustained release formulation.

The present invention also provides for a method of treatment of pain in mammals, including humans. The method comprises administering a pharmaceutically effective amount of a peptide of formula 1 or a pharmaceutically acceptable salt or composition thereof in one of the traditional modes e.g. orally, parenterally, transdermally, or transmucosally, in a sustained release formulation using a biodegradable biocompatible polymer, or by on-site delivery using micelles, gels and liposomes. The peptides can be administered to a human patient in a dosage of about 0.01 to 100 mg/kg, preferably about 0.05 to 20 mg/kg and most preferably about 0.1–1 mg/kg.

The following examples are used to better describe the invention. These examples are for the purpose of illustration only, and are not intended to limit the invention in any manner.

EXAMPLE 1

Preparation of 1C H-Tyr-D-Ala-Phe(p-F)-Phe-$NH_2$

The synthetic peptide was prepared using Knorr resin. The amino acids used had their alpha amino group Fmoc-protected and Tyrosine side chain tBu protected. Dimethylformamide used in the coupling step was free of dimethylamine. DMF used for the washing steps and TFA were Biograde purity. For the purification step USP purified $H_2O$ and acetonitrile of HPLC grade were used. All remaining solvents were of ACS purity and used as such without any purification.

Solid phase synthesis was carried out manually on the resin having a load of 0.84 mMoles/g. Peptide condensation was carried out using 1.5 to 2 equivalents each of Fmoc-amino add, HOBT and BOP in DMF for 3–24 hours at room temperature. The alpha amino Fmoc deprotection steps were performed using 20% (v/v) Piperidine in DMF for 25 minutes. The peptide cleavage and side chain deprotection were accomplished by treatment with TFA/$CH_2Cl_2$/anisole. The peptide resin was treated with TFA for two periods of 90 minutes at room temperature under nitrogen atmosphere. After $CH_2Cl_2$ washing and evaporation the residue was treated with ethyl ether, the precipitate filtered and dried under vacuum.

The crude peptide obtained was purified by HPLC on a $C_{18}$ 10$\mu$–15$\mu$ 300 A reverse phase column, with a gradient elution using 0.06% TFA/$H_2O$ and 0.06% TFA/Acetonitrile. Monitoring was performed at 220 nm. Pure fractions were pooled and lyophilized. The purified material was exchanged into its hydrochloride salt form to give the pure title compound.

In a like manner the following peptides were also synthesized:

1A H-Tyr-D-Ala-Phe-Phe-$NH_2$
1B H-Tyr-D-Ala-Phe(p-F)-Phe(p-F)-$NH_2$

EXAMPLE 2

Preparation of 2C H-Tyr-D-Arg-Phe(p-F)-Phe-$NH_2$

The synthetic peptide was prepared using Knorr resin. The amino acids used had their Alpha amino group Fmoc-protected and the following side chains protected: (Pmc) for D-Arginine, and tBu for Tyrosine. Dimethyformamide used in the coupling step was free of dimethylamine. DMF used for the washing steps and TFA were Biograde purity. For the purification step USP purified $H_2O$ and acetonitrile of HPLC grade were used. All remaining solvents were of ACS purity and used as such without any purification.

Solid phase synthesis was carried out manually on the resin with a load of 0.84 mMoles/g. Peptide condensation was carried out using 2 equivalents each of Fmoc-amino acid, HOBT and BOP in DMF for 2–5 hours at room temperature. The alpha amino Fmoc deprotection steps were performed using 20% (v/v) Piperidine in DMF for 25 minutes. The peptide cleavage and side chain deprotection were accomplished by TFA/$CH_2Cl_2$/Anisole treatment. The peptide resin treated with TFA for two periods of 90 minutes at room temperature under nitrogen atmosphere. After $CH_2Cl_2$ washing and evaporation the residue was treated with ethyl ether, the precipitate filtered and dried under vacuum.

The crude peptide obtained was purified by HPLC on a $C_{18}$ 10$\mu$–15$\mu$ 300 A reverse phase column, with a gradient elution using 0.06% TFA/$H_2O$ and 0.06% TFA/Acetonitrile. Monitoring was performed at 220 nm. Pure fractions were pooled and lyophilized.

In a like manner the following peptide compounds were synthesized:

2A H-Tyr-D-Arg-Phe-Phe-$NH_2$
2B H-Tyr-D-Arg-Phe(p-F)-Phe(p-F)-$NH_2$

EXAMPLE 3

Radioligand Binding Assay
MEMBRANE PREPARATION

Male Sprague-Dawley rats weighing between 350–450 g were sacrificed by inhalation of $CO_2$. The rats were decapitated and the brains minus cerebellum were removed and place in ice-cold saline solution and then homogenized in ice-cold 50 mM Tris buffer pH 7.4 (10 ml/brain). The membranes were centrifuged at 14000 rpm for 30 min. at 4° C. The pellets were re-suspended in approximately 6 ml/brain of ice-cold Tris buffer 50 mM pH 7.4 and stored at −78° C. until ready for use. Protein quantification of the brain homogenate was conducted according to protein assay kit purchased (Bio-Rad).
RADIOLIGAND INHIBITION ($^3$H)- DAMGO and ($^3$H) DAGLE were used as radioligands for the $\mu$ and $\delta$ receptors, respectively. Radioligand 50 $\mu$l, membranes 100 $\mu$l and serially diluted test compound were incubated for 1 hr at 22° C. Non specific binding was determined using 500 fold excess of unlabeled ligand in the presence of tracer and membranes. Free ligand was separated from bound by filtration through Whatman GF/B paper (presoaked in polyethylenimine 1% aqueous solution) and rinsing with ice-cold 50 mM Tris pH 7.4 using a Brandel cell harvester. The filters were dried and radioactivity was counted in a 24 well microplate in the presence of 500 ml scintillant per well. Radioactivity was measured using a Wallac 1450 Microbeta counter.

Ki's for the various compounds were determined from the $IC_{50}$ according to the Cheng and Prusoff equation. Results of the binding assay are summarized in table 1.

The activity of the peptide compounds on $\mu$ receptors was determined using the Guinea Pig Ileum (GPI) assay (longitudinal muscle preparation) according to the procedures described in Schiller et al., *Biophys. Res. Commun.*, 85, p.1322 (1975). Activity results are summarized in table 1.

EXAMPLE 4

Hot Plate Assay (measurement of analgesic activity) Conducted at 55° C.

For this assay, CD #1 male mice weighing between 20 and 25 g were used. The mice were weighed, marked, and divided into groups of 10.

The mice were treated by subcutaneous injection of the compound (or the standard or the medium) in an injection volume equivalent to 0.1 ml/10 g p.c. (10 ml/kg).

The mice were individually evaluated for reaction time on the hot plate. The temperature of the hot plate (Sorel, model DS37) was set at 55° C. The mouse was observed for signs of discomfort such as licking or shaking of the paws, attempting to escape (jumping off the plate) or trembling. The reaction time was counted when one of these signs appeared and was noted in "seconds". Each mouse was observed for a maximum period of 30 seconds so as to prevent damage to the paw tissue.

Figure 1:
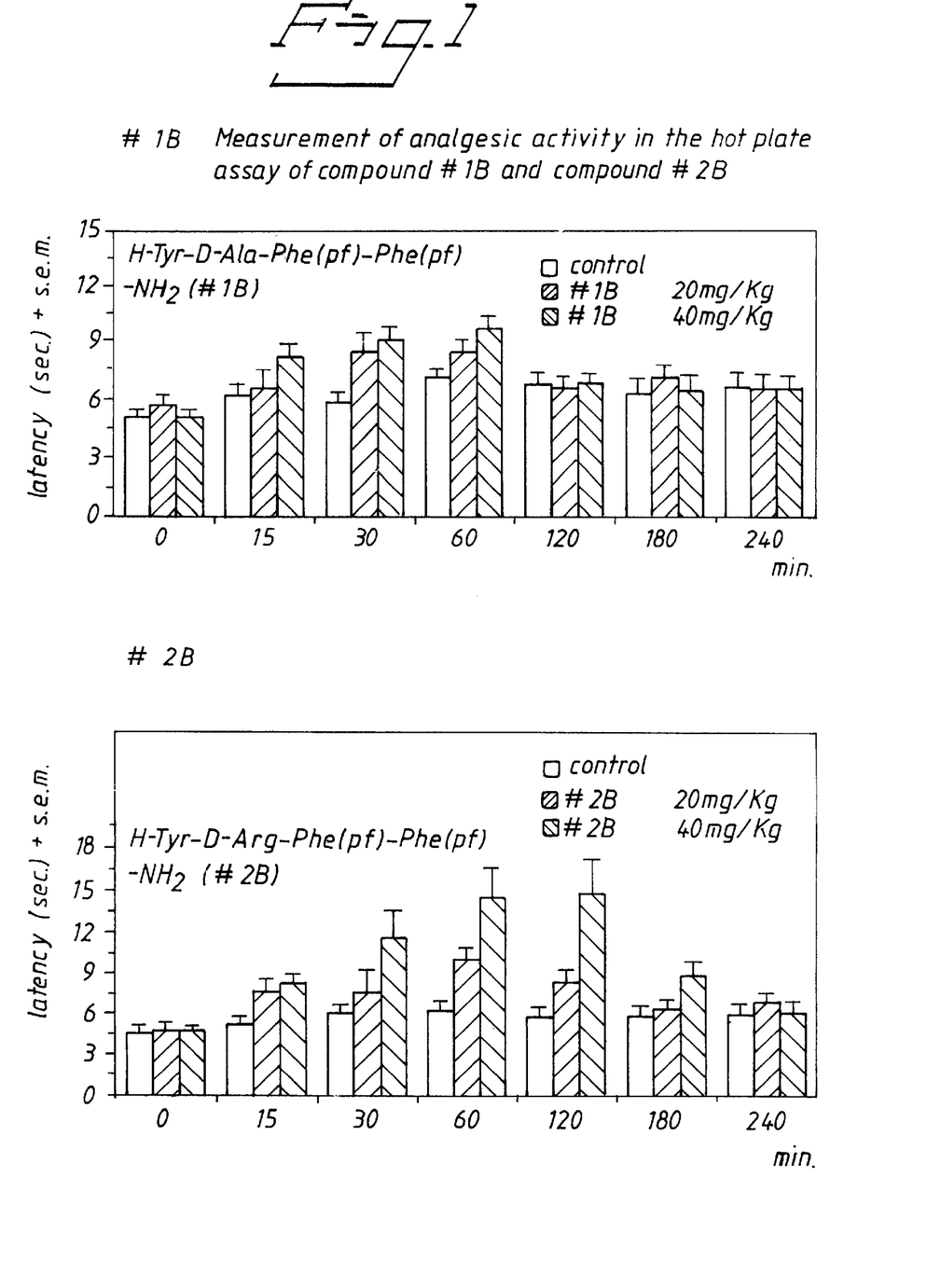
FIGS. 1, 2, and 4 illustrate the inhibitory effect of compounds of the invention in two different hot-plate assays.
Figure 2:
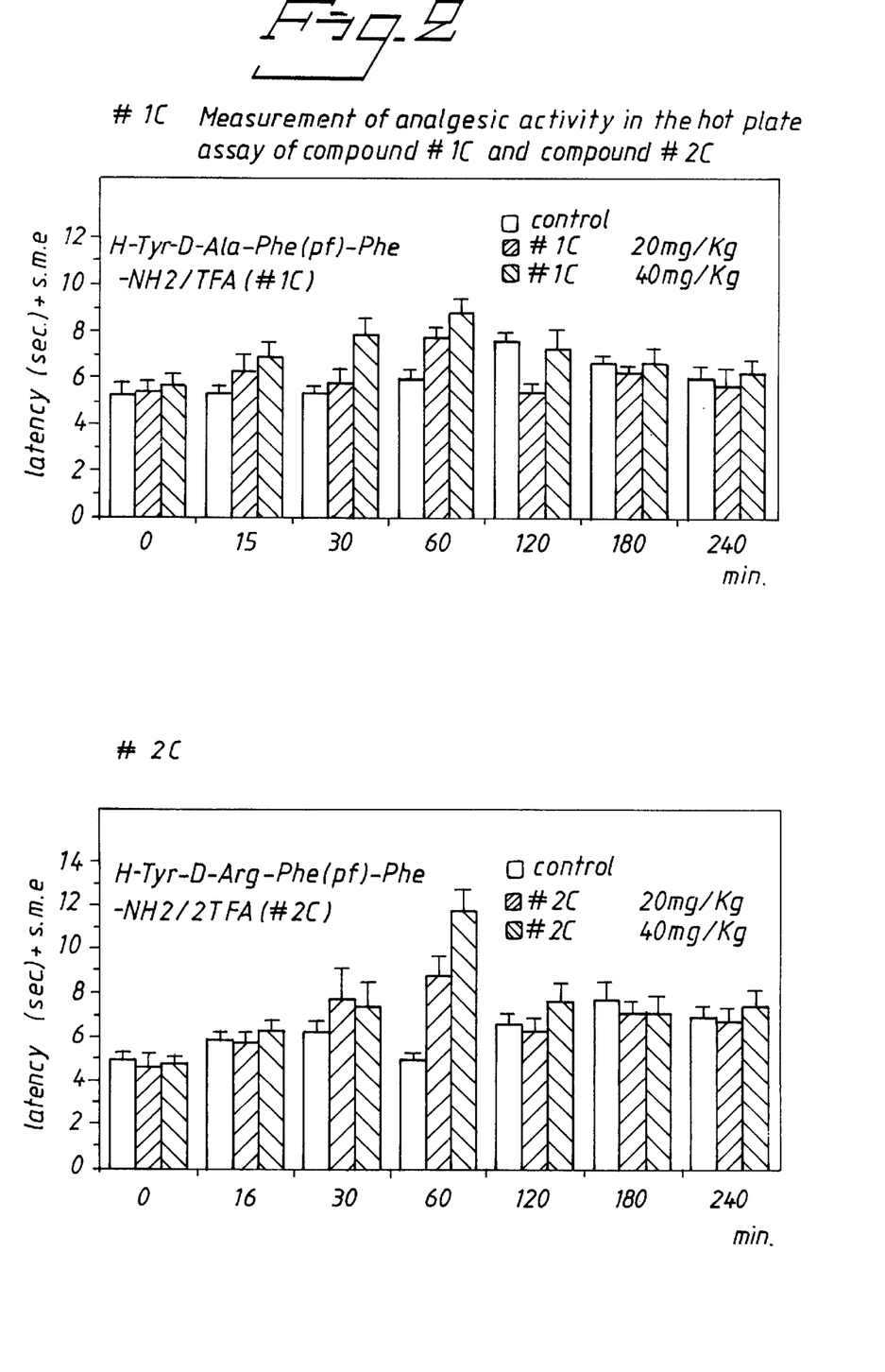
Figure 3:
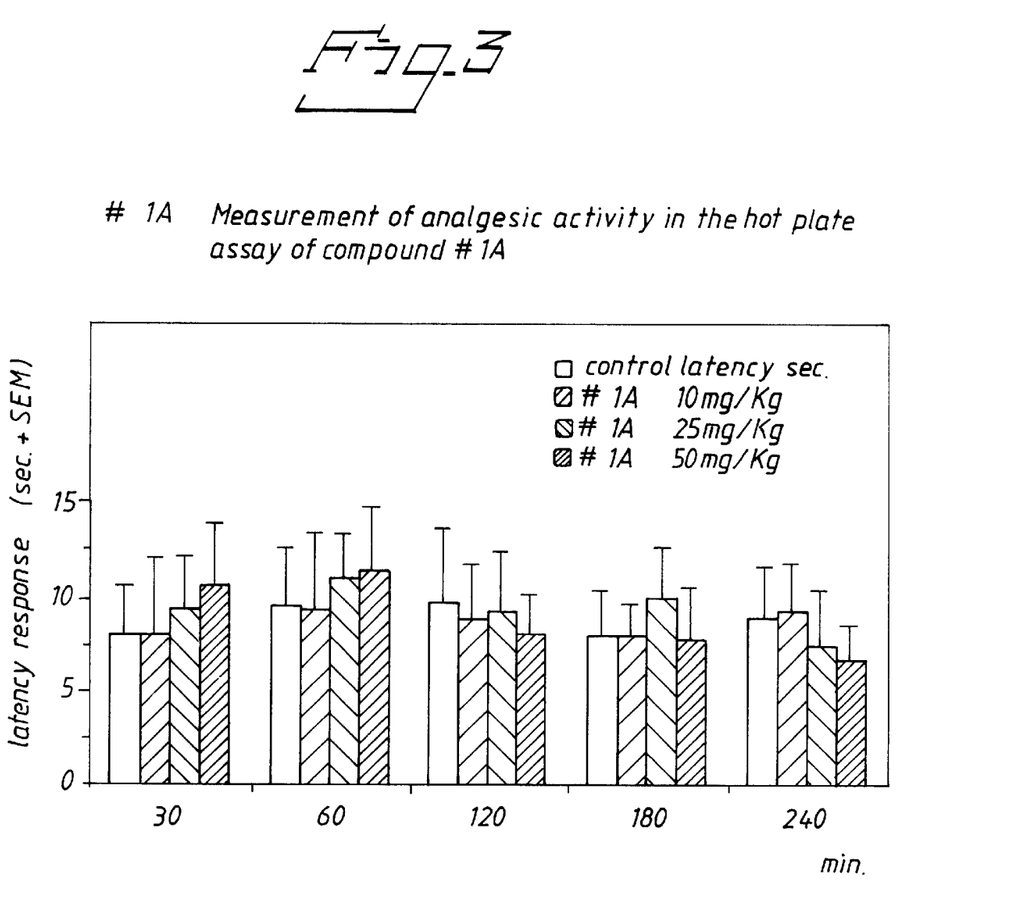
FIG. 3 illustrate the inhibitory effect of H-Tyr-D-Ala-Phe-Phe-NH$_2$ in a hot-plate assay.

For each time reading, the average reaction time of the control group was multiplied by 1.5. The reaction time of each treated mouse was compared to the "control average× 1.5". If the reaction time was inferior to the "control average×1.5", the mouse was considered to not have had an analgesic effect. If the reaction time was superior to the "control average×1.5", then the mouse was considered to have had an analgesic effect. The number of analgesic mice in a group determined the analgesic percentage of the compound for this reading. If the analgesic percentage was inferior to 30%, the compound was considered inactive. The results are shown on FIGS. 1 to 3.

EXAMPLE 5

Writhing Assay

The test was performed on CD #1 male mice weighing between 18 and 22 g. The mice were weighed and marked. They were injected, by intra-peritoneal route, with 0.3 ml/20 g by weight with a solution of phenylquinone at 0.02%. The contortions which appeared during a 15 minute time period following the injection were counted. The phenylquinone was injected at time intervals of 5, 20 or 60 minutes after administration of the compound (or medium, or standard) by subcutaneous route.

The 0.02% phenylquinone** solution was prepared in the following fashion. 20 mg of phenylquinone was dissolved in 5 ml ethanol 90% (sigma, reagent, alcohol).

** 2-phenyl-1,4-benzoquinone (Sigma)

The dissolved phenylquinone was slowly added to 95 ml of distilled water continuously shaken and preheated (not boiled). The phenylquinone solution was left 2 hours before use, and at all times, protected from light. A new solution was prepared every day for the test.

Results of the assays are summarized below in table 1. It can be seen that peptide compounds of the invention wherein either one or both of $R_3$ and $R_4$ are Phe(p-F) exhibit greater selectivity for the $\mu$ opioid receptor compared to the corresponding compound without Phe(p-F) as well as greater transduction of the receptor as determined in the GPI assay. Further, compounds of the invention exhibit greater peripheral analgesic activity as determined in the writhing assay.

TABLE 1

| | Binding Assay | | | Writhing | GPI |
|---|---|---|---|---|---|
| Example | $K_i^\mu$ (nM) | $K_i^\delta$ (nM) | $K_i^\delta/K_i^\mu$ | $ED_{50}$ (mg/kg) | $IC_{50}$ (nM) |
| 1A | 1.53 | 625.8 | 409 | 1.4 | 3 |
| 1B | 0.2 | 199.6 | 998 | 0.2 | 0.12 |
| 1C | 0.36 | 201.2 | 559 | 0.5 | |
| 2A | 0.68 | 1652.6 | 2430 | 0.5 | 6.7 |

TABLE 1-continued

| | Binding Assay | | | Writhing | GPI |
|---|---|---|---|---|---|
| Example | $K_i^\mu$ (nM) | $K_i^\delta$ (nM) | $K_i^\delta/K_i^\mu$ | $ED_{50}$ (mg/kg) | $IC_{50}$ (nM) |
| 2B | 0.22 | >1000 | | 0.3 | |
| 2C | 0.57 | 952.5 | 1671 | 0.3 | 1.52 |

EXAMPLE 6

Hot Plate Assay (measurement of analgesic activity) Conducted at 58° C.

For this assay, NMR1 male mice weighing between 20 and 25 g were used. The mice were weighed, marked, and divided into groups of 6.

The mice were treated by subcutaneous injection of the compound (or the standard or the medium) in an injection volume equivalent to 0.1 ml/10 g p.c. (10 ml/kg).

The mice were individually evaluated for reaction time on the hot plate. The temperature of the hot plate (IITC, Inc; Model 35-0) was set at 58° C. The mouse was observed for signs of discomfort such as licking or shaking of the paws, attempting to escape (jumping off the plate) or trembling. The reaction time was counted when one of these signs appeared and was noted in "seconds". Each mouse was observed for a maximum period of 20 seconds so as to prevent damage to the paw tissue.

The compound was considered analgesic if the reaction time was significantly different (p<0.05; two way ANOVA, sigma slot) from the control group.

Figure 4:
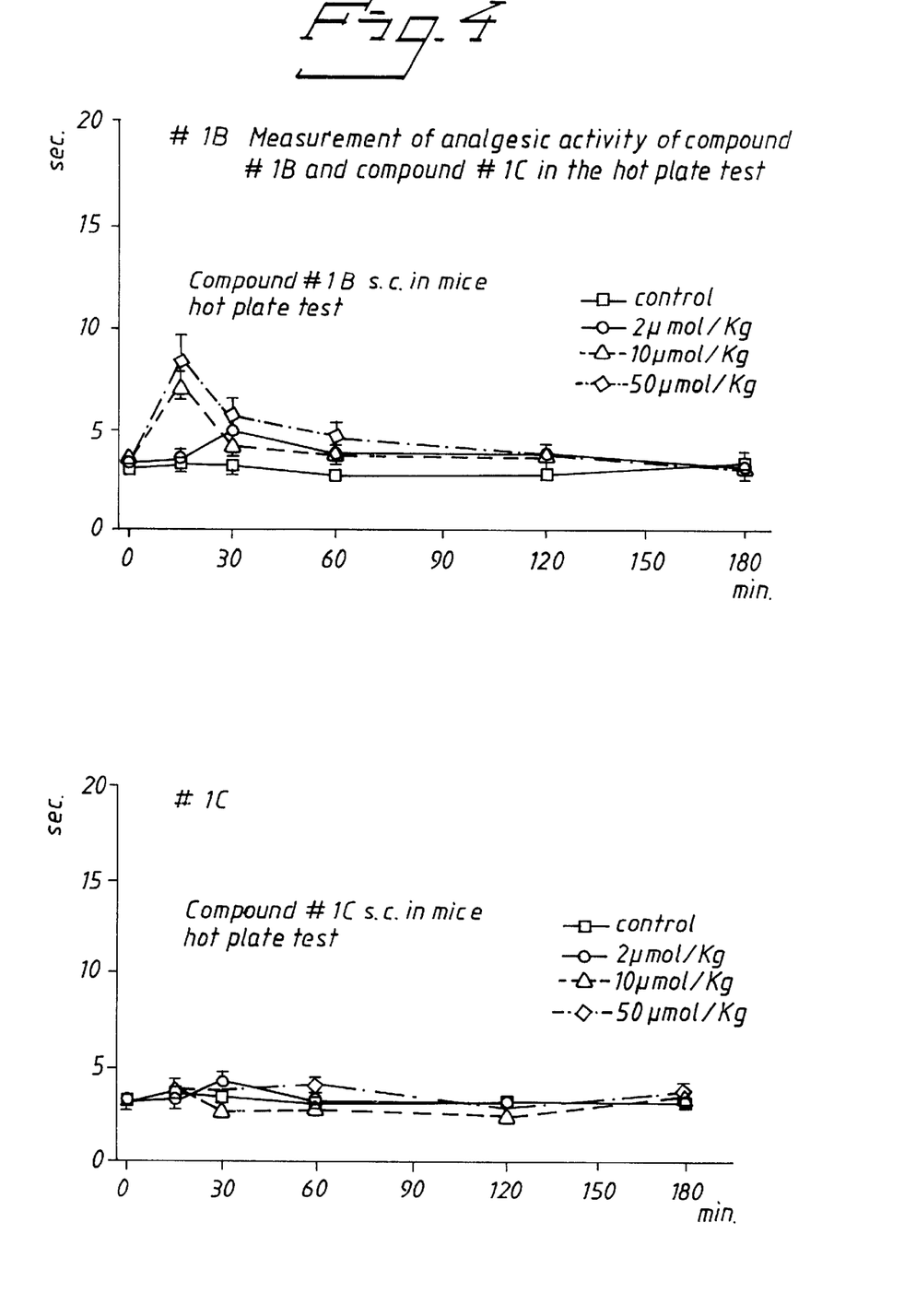

The results are shown of FIG. 4.

EXAMPLE 7

TAIL FLICK ASSAY

For this assay, NMRI male mice weighing between 20 and 25 g were used. The mice were weighed, marked, and divided into group of 6.

The mice were treated by subcutaneous injection of the compounds (or the standard medium) in an injection volume equivalent to 0.1 ml/10 gp.c (10 ml/kg). The mice were individually evaluated for reaction time in the tail flick test. The latency to the flick of the tail was measured when a rheostat-controlled light beam was directed at the tip of he tail (IITC Inc. Model 33). Each mouse was observed for a maximum period of 10 seconds so as to prevent damage to the tissue.

The compound was considered to be analgesic if the reaction time was significantly different (p<0.05, two way ANOVA, Sigma Stat) from the control group.

Figure 5:
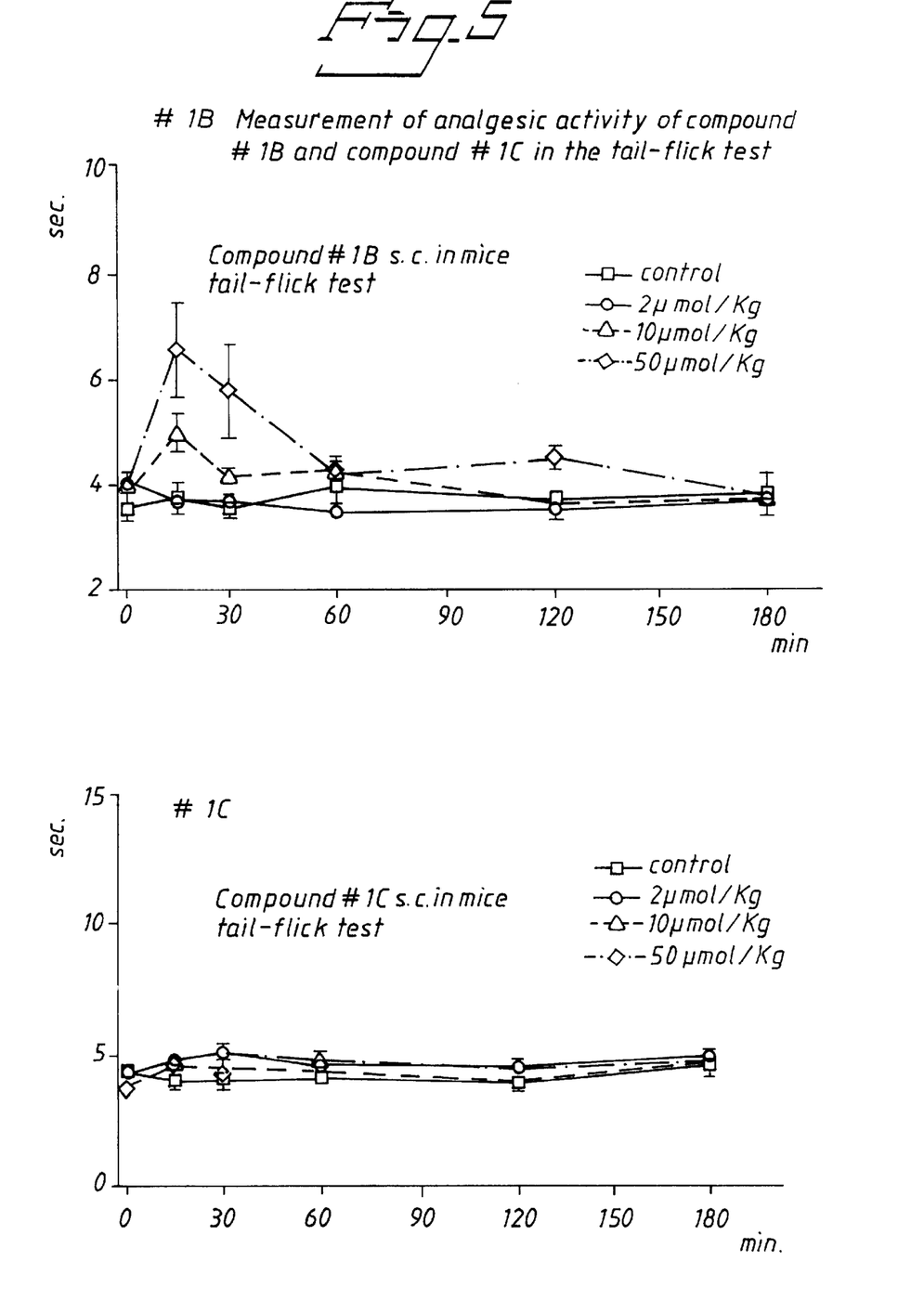
FIG. 5 illustrate the inhibitory effect of compounds of the invention in the tail-flick assay.

The results are shown in FIG. 5.

What is claimed is:

1. A compound of the formula (1):

and salts, thereof
wherein,
   $R_1$ is Tyr or 2',6'-dimethyltyrosine, or an analog or derivative thereof;

$R_2$ is D-Ala or D-Arg;
$R_3$ is Phe(p-F);
$R_4$ is Phe or Phe(p-F);
X is H or $C_{1-6}$alkyl; and
Y and Z are independently H, aralkyl or $C_{1-6}$alkyl.

2. The compound according to claim 1, wherein $R_2$ is D-Ala.

3. The compound according to claim 1, wherein $R_2$ is D-Arg.

4. The compound according to claim 1, $R_4$ is Phe.

5. The compound according to claim 4, wherein $R_2$ is D-Ala.

6. The compound according to claim 4, wherein $R_2$ is D-Arg.

7. The compound according to claim 1 wherein X is H, and Y and Z are both H.

8. The compound according to claim 1, selected from:
H-Tyr-D-Ala-Phe(p-F)-Phe(p-F)-NH$_2$; and
H-Tyr-D-Ala-Phe(p-F)-Phe-NH$_2$.

9. The compound H-Tyr-D-Ala-Phe(p-F)-Phe-NH$_2$.

10. The compound according to claim 1, selected from:
H-Tyr-D-Arg-Phe(p-F)-Phe(p-F)-NH$_2$; and
H-Tyr-D-Arg-Phe(p-F)-Phe-NH$_2$.

11. The compound H-Tyr-D-Arg-Phe(p-F)-Phe-NH$_2$.

12. A pharmaceutical composition comprising a compound of claim 1 in admixture with a pharmaceutically acceptable carrier.

13. A pharmaceutical composition comprising a compound according to claim 7, in admixture with a pharmaceutically acceptable carrier.

14. A method for the treatment of pain comprising, administering to a mammal in need of such treatment a pharmaceutically effective amount of a compound according to claim 1.

15. A method for the treatment of pain comprising, administering to a mammal in need of such treatment a pharmaceutically effective amount of a compound according to claim 7.

* * * * *